United States Patent [19]

Fried

[11] Patent Number: 5,136,102

[45] Date of Patent: Aug. 4, 1992

[54] PROCESS FOR THE PREPARATION OF KETONES

[75] Inventor: Herbert E. Fried, Houston, Tex.

[73] Assignee: Shell Oil Company, Houston, Tex.

[21] Appl. No.: 779,454

[22] Filed: Oct. 18, 1991

[51] Int. Cl.$^5$ .................................................. C07C 45/29
[52] U.S. Cl. .................................................. 568/402
[58] Field of Search ........................................ 568/402

[56] References Cited

PUBLICATIONS

Cella et al., J. Org. Chem., vol. 40, pp. 1860–1862 (1975).

Semmelhack et al., "Oxidation of Alcohols to Aldehydes with Oxygen and Cupric Ion, Mediated by Nitrosonium Ion," J. Am. Chem. Soc. 1984, 106, 3374–3376.

Yamaguchi et al., "Application of Redox System Based on Nitroxides to Organic Synthesis," Pure & Applied Chemistry, vol. 62(2), 1990, pp. 217–222.

*Primary Examiner*—James H. Reamer

[57] ABSTRACT

A process for the preparation of a ketone which comprises reacting the corresponding secondary alkanol with a solubilized stable free radical nitroxide having the formula:

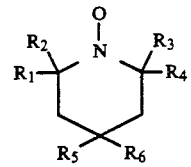

wherein each of $R_1$, $R_2$, $R_3$ and $R_4$ is an alkyl, aryl or heteroatom substituted alkyl group having 1 to about 15 carbon atoms and each of $R_5$ and $R_6$ is alkyl, hydrogen, aryl or a substituted heteroatom, nitric acid, and a bromide ion-containing compound in the presence of an oxidant at a temperature in the range of from about $-10°$ C. to about 60° C. and thereafter separating out the ketone.

16 Claims, No Drawings

PROCESS FOR THE PREPARATION OF KETONES

FIELD OF THE INVENTION

This invention relates to a process for the preparation of ketones by the oxidation of the corresponding secondary alkanols in the presence of a stable free radical nitroxide, nitric acid, a bromide ion-containing compound and an oxidant.

BACKGROUND OF THE INVENTION

It is known to use nitroxyl radicals/oxoammonium salts in the oxidation of primary alcohols to produce aldehydes and acids and secondary alcohols to ketones (*Journal of Organic Chemistry*, vol. 52 (12), pp. 2559-2562 and *Journal of Organic Chemistry*, vol. 55, 1990, pp. 462-466). The primary products produced in these processes are aldehydes and the stoichiometrically consumed oxidant is hypochlorite.

It is reported in the open literature that primary aliphatic alcohols can be converted to aldehydes in 30-40% yields in the presence of catalytic amounts of cuprous chloride, 2,2,6,6,-tetramethylpiperidine-1-oxyl, and atmospheric oxygen (*Journal of American Chemical Society*, 1984, 106, pp. 3374). It is also known that higher yields of aldehydes can be obtained if stoichiometric amounts of cupric or ferric salts are used instead of catalytic amounts of the cuprous salts (*Pure and Applied Chemistry*, vol. 62(2), 1990, pp. 217-222).

OBJECTS OF THE INVENTION

It is an object of this invention to produce ketones in high yields and with high selectivities at increased rates from secondary alkanols.

It has been found that in the oxidation of secondary alkanols to ketones, dramatically increased reaction rates and higher yields of ketones can be obtained when catalytic amounts of a bromide ion-containing compound are used in combination with a stable free radical nitroxide, nitric acid, and an oxidant.

SUMMARY OF THE INVENTION

This invention relates to a process for the preparation of a ketone which comprises reacting the corresponding secondary alkanol with a solubilized stable free radical nitroxide having the formula:

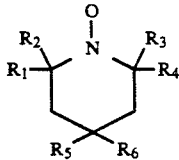

wherein each of $R_1$, $R_2$, $R_3$ and $R_4$ is an alkyl, aryl or heteroatom substituted alkyl group having 1 to about 15 carbon atoms and each of $R_5$ and $R_6$ is alkyl, hydrogen, aryl or a substituted heteroatom, nitric acid and a bromide ion-containing compound in the presence of an oxidant at a temperature in the range of from about $-10°$ C. to about $60°$ C. and thereafter separating out the ketone.

DESCRIPTION OF THE PREFERRED EMBODIMENTS

The present process converts secondary alkanols to the corresponding ketones by contacting the secondary alkanol with a solubilized stable free radical nitroxide and nitric acid in the presence of a bromide ion-containing compound and an oxidant at a temperature in the range of from about $-10°$C. to about $60°$ C.

The secondary alkanol reactant suitably comprises one or more secondary alkanols having a carbon number in the range of from about 3 to about 45. An secondary alkanol consisting essentially of secondary, mono-alkanols is preferred. Most preferably, the secondary alkanol reactant consists essentially of one or more $C_6$ to $C_{30}$ secondary mono-alkanols. Preference can also be expressed for secondary alkanols having from 8 to about 22 carbon atoms, with $C_{10}$ to $C_{20}$ secondary alkanols considered more preferred and $C_{11}$ to $C_{18}$ secondary alkanols considered most preferred. As a general rule, the carbon chains o the secondary alkanols may be of either branched or linear (straight-chain) structure, although preference further exists for secondary alkanol reactants in which greater than about 50 percent, more preferably greater than about 70 percent and most preferably greater than about 90 percent of the molecules are of linear (straight-chain) carbon structure. In large part, such preferences relate more to the utility and value of the products than to the operability or performance of the process of the invention.

The general suitability of such secondary alkanols as reactants in oxidation reactions is well recognized in the art. Examples of specific secondary alkanols and commercially available secondary alkanols and secondary alkanol mixtures within this class are also well known. Commercially available mixtures of secondary alkanols prepared via the oxidation of paraffins, and from internal olefins and alpha-olefin mixtures via sulfation and hydrolysis reactions are particularly suitable.

Suitable examples of $C_{10}$ to $C_{20}$ secondary alkanols for use in the present invention which are commercially available include Tergitol 15, a trademark of and sold by Union Carbide in which the main components are $C_{11}$ to $C_{15}$ compounds., Tergitol 45, in which the main components are $C_{14}$ to $C_{15}$ compounds; Softanol 24, a trademark of and sold by Nippon Shokubai Kagaku Kogyo Co., Ltd., in which the main components are $C_{12}$ to $C_{14}$ compounds, and the like. Examples of suitable secondary alkanols having lower carbon numbers include isopropanol, 2-butanol, 2-pentanol, 3-pentanol, 2-hexanol, 3-hexanol, 2-octanol, 3-octanol and the like.

The term "stable free radical nitroxide" as used herein shall mean a free radical nitroxide that can be prepared by conventional chemical methods and will exist long enough to be used in a subsequent chemical reaction or examined in a static system by normal methods of spectroscopy. Generally, the stable free radical nitroxides of the present invention have a half life of at least one year. The term "stable free radical" shall also be understood to include the precursor to a stable free radical from which the stable free radical may be produced in situ.

The stable free radical nitroxides, as used in the present process, are precursors to catalysts, i.e., oxoammonium salts, active for the oxidation of secondary alkanols to the corresponding ketones. These catalysts are generated in situ by the oxidation of a stable free radical nitroxide to an oxoammonium salt with an oxygen-containing oxidant. The stable free radical nitroxide can be obtained by the oxidation of secondary amines or hydroxylamines.

The stable free radical nitroxides which are suitable for use in the instant invention have the formula:

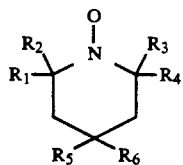

wherein each of $R_1$, $R_2$, $R_3$ and $R_4$ is an alkyl, aryl or heteroatom substituted alkyl group having 1 to about 15 carbon atoms and no hydrogen is bound to the remaining valences on the carbon atoms bound to the nitrogen, and each of $R_5$ and $R_6$ is alkyl, hydrogen, aryl or a substituted heteroatom. As used herein, the term "alkyl" is meant to include cycloalkyl. The alkyl (or heteroatom substituted) groups $R_1$-$R_4$ may be the same or different, and preferably contain 1 to 15 carbon atoms. Preferably, $R_1$-$R_4$ are methyl, ethyl, or propyl groups. In addition to hydrogen, the heteroatom substituents may include, halogen, oxygen, nitrogen and the like. Preferably, one of $R_5$ and $R_6$ is hydrogen with the other one being a substituted heteroatom which does not interfere with the reaction. Suitable substituted heteroatoms include —OR,

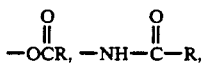

—NMe$_3$Cl$^-$, —O—SO$_3$H, —O— polymer and the like.

In a preferred embodiment, the nitroxide is selected from the group consisting of 2,2,6,6-tetramethyl-piperidine-1-oxyl, 4-hydroxy-2,2,6,-tetramethyl-piperidine-1-oxyl, 4-oxo-2,2,6,6-tetramethyl-piperidine-1-oxyl, 2,2,6,6-tetramethyl-piperidine-1-oxyl-4-sulfate, 4-alkoxy-2,2,6,6-tetramethyl-piperdine-1-oxyl and mixtures thereof, with 2,2,6,6-tetramethylpiperidine-1-oxyl, 2,2,6,6-tetramethyl-piperidine-1-oxyl-4-sulfate, and 4-alkoxy-2,2,6,6-tetramethyl-piperidine-1-oxyl being particularly preferred.

As used herein, "nitric acid" refers to nitric acid, fuming nitric acid, or nitrous acid generated by contacting alkali metal nitrite with mineral acid. The nitric acid suitable for use in the present invention typically has a concentration in the range of from about 50 percent to about 100 percent, preferably about 70 percent. Generally, an amount of nitric acid in the range of from about 5 mole percent to about 100 mole percent, basis the number of moles of starting secondary alkanol is used. The nitric acid is typically added to the reaction mixture after all of the other reactants have been added. While not wishing to be bound by any particular theory, it is believed that nitrogen oxides (NO$_x$) are generated in the reaction and are the active species in the reaction.

The bromide ion-containing compound in the present invention can be any ionic bromide which is in a soluble form. The presence of bromide ion is critical to the instant process as it dramatically increases the rate of the reaction. In addition, the bromide ion stabilizes the nitroxide so that deoxygenation to the corresponding secondary amine is substantially minimized. As a result, less nitroxide can be used to achieve the desired conversions. The bromide ion is suitably introduced into the process as a quaternary alkyl bromide such as, for example, ammonium bromide, a tetraalkyl ammonium bromide such as, for example, tetramethyl ammonium bromide, an alkali metal bromide such as for example, sodium bromide, potassium bromide, lithium bromide, calcium bromide and the like. In a preferred embodiment, the bromide ion-containing compound is selected from the group consisting of ammonium bromide, sodium bromide, potassium bromide and mixtures thereof, with potassium bromide being particularly preferred.

The oxidants suitable for use in the instant invention are those compounds which are capable of oxidizing the stable free radical nitroxide to the oxoammonium salt. Suitable oxidants include oxygen or an oxygen-containing gas such as air. Whereas pure oxygen is preferred to accomplish the desired conversion, the oxygen can also be diluted with an inert gas such as nitrogen, helium, argon, or other similar gas. While air can be used as the oxidant, the reaction rate can be slower. For purposes of increasing the reaction rate, higher O$_2$ pressures such as, for example, 1000 psi can be utilized. In a preferred embodiment, pure oxygen is used as the oxidant and it is bubbled into the reaction solution at atmospheric pressure. It is critical that the flow of the oxidant or oxygen-containing gas be continuous throughout the process in order to keep the reaction going. If the flow of oxygen is stopped during the course of the reaction, the reaction rate is significantly reduced.

The reaction in the instant invention can be carried out in the presence or absence of a solvent. When the reaction is carried out in the presence of a solvent, the solvent is generally a solvent in which the secondary alkanol is readily soluble. Solvents which are most suitable are those which are inert in the reaction. The solvent may be added to the reaction mixture, or alternatively, the nitroxide may be dissolved in the solvent prior to addition of the nitroxide to the reaction medium. The solvent is typically selected from the group consisting of acetonitrile, ethyl acetate, tertiary alcohols such as tertiary butyl alcohol, hydrocarbons such as heptene, dichloromethane, chlorobenzene, glyme and mixtures thereof. In a preferred embodiment, the solvent is selected from dichloromethane and tertiary butyl alcohol. The amount of solvent utilized in the process is typically in the range of from about 20:1 to about 0.5:1, preferably from about 10:1 to about 5:1, basis the weight of the starting secondary alkanol.

The amounts and concentrations of the reactants utilized in the process of the instant invention can vary within wide ranges. The amount of stable free radical nitroxide is typically in the range of from about 1 mole percent to about 50 mole percent, preferably from about 5 mole percent to about 30 mole percent, basis the number of moles of starting secondary alkanol. Generally, the amount of nitric acid utilized will be in the range of from about 5 mole percent to about 100 mole percent, preferably from about 25 mole percent to about 50 mole percent, basis the starting secondary alkanol. Generally, the bromide ion-containing compound is present in an amount sufficient to catalyze the reaction. Typically, the amount of bromide ion-containing compound is about 6 mole percent, basis the starting secondary alkanol.

The process of the present invention is typically conducted under mild conditions, with good results being obtained using a temperature in the range of from about −10° C. to about 60° C., preferably about 20° C. to about 35° C., and more preferably about 25° C. to about 30° C. Reaction pressures are not critical although higher pressures result in increased reaction rates. Pressures in the range of from about atmospheric pressure up to about 1000 psig can be employed with good results.

The process of the instant invention can be carried out either batchwise or continuously, using a stirrer equipped reactor or other well known contacting technique to achieve adequate mixing. Preferred reaction conditions, e.g., temperature, pressure, flow rates, etc., vary somewhat depending on the specific nitroxide utilized and on the concentration of the nitroxide.

The process of the instant invention can be carried out in a variety of ways. For example, 0.032 moles of secondary alkanol, 0.006 moles of the nitroxide, and 0.002 moles of bromide ion-containing compound may be added to the reaction vessel, followed by the addition of 0.016 moles of nitric and $O_2$. Alternatively, the secondary alkanol, the nitroxide, the nitric acid, and the bromide ion-containing compound and the oxidant may be added simultaneously to the reaction vessel and allowed to reach equilibrium. In a preferred embodiment, the reaction is carried out by adding the secondary alkanol, the nitroxide, and the bromide ion-containing compound together with the solvent, if one is used, and thereafter adding the nitric acid and bubbling an oxidizing gas through the mixture. Following the reaction, the product may be separated from the reaction mixture using conventional procedures such as extraction using a suitable extraction solvent such as, for example, ethyl acetate; evaporation wherein the solvent is stripped from the reaction mixture by using heat or vacuum. The reaction product can be purified by a number of conventional means such as, for example, distillation or by other means known to those skilled in the art.

Depending upon process conditions and the nitroxide used, the yields of ketone obtained by this invention are at least about 90% of starting secondary alkanol material being converted. The products produced by the instant process can be used in a variety of applications. For example, these products can be used as solvents, or as intermediates to produce amines or ethers.

The ranges and limitations provided in the instant specification and claims are those which are believed to particularly point out and distinctly claim the present invention. It is, however, understood that other ranges and limitations which perform substantially the same function in the same or substantially the same manner to obtain the same or substantially the same result are intended to be within the scope of the instant invention as defined by the instant specification and claims.

The process of this invention will be further described by the following embodiments which are provided for illustration and are not to be construed as limiting the invention.

ILLUSTRATIVE EMBODIMENTS

EXAMPLE 1

4.2 Grams of 2-octanol, 1 gram of 2,2,6,6-tetramethylpiperidine-1-oxyl, 25 milliliters of acetonitrile, and 0.25 grams of potassium bromide dissolved in 1 gram of water, were charged to a 100 milliliter round bottomed flask. To this mixture was added 1 gram of 70% nitric acid. An $O_2$ stream was then bubbled through the reaction mixture. The reaction was held at room temperature over a 4 hour period. The results are presented in Table I.

EXAMPLE 2

4.2 Grams of 2-octanol, 1 gram of 2,2,6,6-tetramethylpiperidine-1-oxyl, 25 milliliters of tertiary butyl alcohol and 0.25 grams of potassium bromide dissolved in 1 gram of water were charged to a 100 milliliter round bottomed flask. To this mixture was added 1 gram of 70% nitric acid. An $O_2$ steam was then bubbled through the reaction mixture. The reaction was held at a temperature of 35° C. over a 5 hour period. The results are presented in Table I.

COMPARATIVE EXAMPLE A

Comparative Example A was carried out in a manner similar to Example 1 except that no bromide ion-containing compound was used. The results are presented in Table I.

COMPARATIVE EXAMPLE B

Comparative Example B was carried out in a manner similar to Example 2 except that no bromide ion was used and the reaction time was 6 hours. The results are presented in Table I.

COMPARATIVE EXAMPLE C

Comparative Example C was carried out in a manner similar to Example 1 except that no nitroxide was used. The results are presented in Table I.

As can be seen in Table I, the bromide ion-containing compound clearly accelerates the reaction rates and the nitroxide is essential for significant oxidation of secondary alcohols to ketones.

TABLE I

| Oxidation Of Secondary Alkanols to Ketones | | |
|---|---|---|
| | % Starting Alkanol Remaining | % Ketones |
| Example 1 | <0.1 | >99.9 |
| Example 2 | <1 | >99 |
| Comparative Example A | 55.6 | 44.4 |
| Comparative Example B | 10.4 | 89.6 |
| Comparative Example C | 96 | 4 |

What is claimed is:

1. A process for the preparation of an ketone which comprises reacting the corresponding secondary alkanol with a solubilized stable free radical nitroxide having the formula:

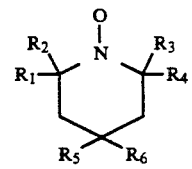

wherein each of $R_1$, $R_2$, $R_3$ and $R_4$ is an alkyl, aryl or heteroatom substituted alkyl group having 1 to about 15 carbon atoms and each of $R_5$ and $R_6$ is alkyl, hydrogen, aryl or a substituted heteroatom, nitric acid, and a bromide ion-containing compound in the presence of an oxidant at a temperature in the range of from about −10° C. to about 60° C. and thereafter separating out the ketone.

2. The process of claim 1 wherein the solubilized stable free radical nitroxide is selected from the group consisting of 2,2,6,6-tetramethyl-piperidine-1-oxyl, 4-hydroxy-2,2,6,6-tetramethyl-piperidine-1-oxyl, 4-oxo-2,2,6,6-tetramethyl-piperidine-1-oxyl, 2,2,6,6-tetramethyl-piperidine-1-oxyl-4-sulfate, 4-alkoxy-2,2,6,6-tetramethyl-piperidine-1-oxyl and mixtures thereof.

3. The process of claim 2 wherein the solubilized stable free radical nitroxide is selected from the group consisting of 2,2,6,6-tetramethyl-piperidine-1-oxyl, 2,2,6,6-tetramethyl-piperidine-1-oxyl-4-sulfate, 4-alkoxy-2,2,6,6-tetramethyl-piperidine-1-oxyl and mixtures thereof.

4. The process of claim 1 wherein the stable free radical nitroxide is dissolved in a solvent selected from the group consisting of acetonitrile, ethyl acetate, tertiary butyl alcohol, dichloromethane, chlorobenzene and mixtures thereof.

5. The process of claim 4 wherein the stable free radical nitroxide is dissolved in a solvent selected from the group consisting of acetonitrile, tertiary butyl alcohol, and mixtures thereof.

6. The process of claim 1 wherein the amount of nitric acid is in the range of from about 5 mole percent to about 100 mole percent, basis the starting secondary alkanol.

7. The process of claim 1 wherein said bromide ion-containing compound is selected from the group consisting of a quaternary alkyl bromide, a tetraalkyl bromide, an alkali metal bromide and mixtures thereof.

8. The process of claim 7 wherein said bromide ion-containing compound is selected from the group consisting of ammonium bromide, sodium bromide, potassium bromide and mixtures thereof.

9. The process of claim 1 wherein said secondary alkanol is contacted with said solubilized stable free radical nitroxide and said bromide ion-containing compound, followed by the addition thereto of said nitric acid and said oxidant.

10. The process of claim 9 wherein the amount of solubilized stable free radical nitroxide is in the range of from about 1 mole percent to about 25 mole percent, basis the number of moles of the secondary alkanol.

11. The process of claim 10 wherein the amount of solubilized stable free radical nitroxide is in the range of from about 5 mole percent to about 20 mole percent, basis the number of moles of the secondary alkanol.

12. The process of claim 1 wherein said oxidant is an oxygen-containing gas.

13. The process of claim 12 wherein said oxygen containing gas is selected from the group consisting of pure oxygen and air.

14. The process of claim 13 wherein said oxygen-containing gas is pure oxygen.

15. The process of claim 1 wherein said process is carried out at a temperature in the range of from about 20° C. to about 35° C. and at atmospheric pressure.

16. The process of claim 15 wherein said process is carried out at a temperature in the range of from about 25° C. to about 30° C. and at atmospheric pressure.

* * * * *